US012661403B2

(12) United States Patent
Avigdor et al.

(10) Patent No.: US 12,661,403 B2
(45) Date of Patent: Jun. 23, 2026

(54) COMPOSITIONS AND METHODS FOR USING ALTERNATING ELECTRIC FIELDS TO DISRUPT LIPID CAPSULES

(71) Applicant: Novocure GMBH, Root (CH)

(72) Inventors: Lilach Avigdor, Haifa (IL); Tali Voloshin-Sela, Haifa (IL); Uri Weinberg, Haifa (IL)

(73) Assignee: Novocure GMBH, Baar (CH)

( * ) Notice: Subject to any disclaimer, the term of this patent is extended or adjusted under 35 U.S.C. 154(b) by 1043 days.

(21) Appl. No.: 17/841,975

(22) Filed: Jun. 16, 2022

(65) Prior Publication Data

US 2023/0000980 A1      Jan. 5, 2023

Related U.S. Application Data

(60) Provisional application No. 63/216,947, filed on Jun. 30, 2021.

(51) Int. Cl.
| | |
|---|---|
| *A61K 9/48* | (2006.01) |
| *A61K 9/127* | (2006.01) |
| *A61K 41/00* | (2020.01) |
| *A61N 1/40* | (2006.01) |

(52) U.S. Cl.
CPC .......... *A61K 41/0028* (2013.01); *A61K 9/127* (2013.01); *A61K 9/4816* (2013.01); *A61N 1/40* (2013.01)

(58) Field of Classification Search
None
See application file for complete search history.

(56) References Cited

U.S. PATENT DOCUMENTS

| | | | |
|---|---|---|---|
| 6,520,950 B1 * | 2/2003 | Hofmann ............. | A61N 1/0412 604/503 |
| 2005/0209642 A1 * | 9/2005 | Palti ...................... | A61N 1/326 607/2 |
| 2021/0178155 A1 | 6/2021 | Hershkovich | |
| 2021/0178173 A1 | 6/2021 | Hershkovich | |

FOREIGN PATENT DOCUMENTS

WO   PCT/IB2022/055587      6/2022

OTHER PUBLICATIONS

Search Report and Written Opinion was issued on Aug. 22, 2022 by the International Searching Authority for PCT Application No. PCT/IB2022/055587, which was filed on Jun. 16, 2022 (Applicant—Novocure GMBH) (Original—11 pages).
U.S. Appl. No. 63/216,947, filed Jun. 30, 2021, Lilach Avigdor (Novocure GMBH).

* cited by examiner

*Primary Examiner* — Celeste A Roney
(74) *Attorney, Agent, or Firm* — Ballard Spahr LLP

(57)      ABSTRACT

Disclosed are methods of delivering a therapeutic to a target site of a subject comprising administering a lipid capsule to a target site of a subject, wherein the lipid capsule comprises a therapeutic agent; and applying an alternating electric field, at a frequency for a period of time, to the target site of the subject, wherein the alternating electric field releases the therapeutic from lipid capsule at the target site of the subject. Disclosed are methods of increasing target site specific release of a therapeutic agent in a subject comprising administering a lipid capsule to a target site of a subject, wherein the lipid capsule comprises a therapeutic agent; and applying an alternating electric field, at a frequency for a period of time, to the target site of the subject, wherein the alternating electric field releases the therapeutic agent from the lipid capsule at the target site of the subject, thereby increasing the target site specific release of the therapeutic agent. Disclosed are methods of treating comprise administering a lipid capsule to a target site of a subject in need thereof, wherein the lipid capsule comprises a therapeutic agent; and applying an alternating electric field, at a frequency for a period of time, to the target site of the subject in need thereof, wherein the alternating electric field releases the therapeutic agent from the lipid capsule at the target site of the subject in need thereof. Disclosed are methods of killing a cell comprising administering a lipid capsule to a target site, wherein the lipid capsule comprises a therapeutic agent; and applying an alternating electric field for a period of time, to the target site, wherein the alternating electric field releases the therapeutic agent from the lipid capsule at the target site, wherein the target site comprises a cell, wherein the therapeutic kills the cell.

20 Claims, No Drawings

COMPOSITIONS AND METHODS FOR USING ALTERNATING ELECTRIC FIELDS TO DISRUPT LIPID CAPSULES

CROSS-REFERENCE TO RELATED APPLICATIONS

This application claims the priority benefit of U.S. Application No. 63/216,947, filed Jun. 30, 2021, that which is hereby incorporated by reference in its entirety.

BACKGROUND

Nanoparticles, including lipid capsules, have been clinically approved for targeted delivery since 1995. They are formulated with a phospholipid bilayer envelop that is a cell-like boundary. This enables liposomes and other nanoparticles a functional scaffold that allows in vivo integration similar to the eukaryotic cell structure.

Tumor Treating Fields, or TTFields, are low intensity (e.g., 1-3 V/cm) alternating electric fields within the intermediate frequency range (e.g., 100-500 kHz) that inhibit cancer cell growth. This non-invasive treatment targets solid tumors and is described in U.S. Pat. No. 7,565,205, which is incorporated herein by reference in its entirety. TTFields are FDA approved for the treatment of glioblastoma (GBM), and may be delivered, for example, via the Optune™ system. Optune™ includes a field generator and two pairs of transducer arrays (i.e., electrode arrays) that are placed on a patient's shaved head. One pair of electrodes is positioned to the left and right of the tumor, and the other pair of electrodes is positioned anterior and posterior to the tumor. In the preclinical setting, TTFields can be applied in vitro using, for example, the Inovitro™ TTFields lab bench system.

TTFields therapy is an approved mono-treatment for recurrent glioblastoma, and an approved combination therapy with chemotherapy for newly diagnosed glioblastoma and unresectable malignant pleural mesothelioma patients. These electric fields are induced non-invasively by transducer arrays (i.e., arrays of electrodes) placed directly on the patient's scalp. TTFields also appear to be beneficial for treating tumors in other parts of the body.

Alternating electrical fields influence dipole moment and thus can disrupt biological membranes. Therefore, administering lipid capsules while applying alternating electrical fields would disrupt phospholipid structure more efficiently at the tumor site where alternating electrical fields are applied leading to targeted treatment of lipid capsules.

BRIEF SUMMARY

Disclosed are methods and compositions for using alternating electric fields to increase permeability of lipid capsules allowing for the release of a therapeutic from inside the lipid capsule.

Disclosed are methods of delivering a therapeutic to a target site of a subject comprising administering a lipid capsule to a target site of a subject, wherein the lipid capsule comprises a therapeutic agent; and applying an alternating electric field, at a frequency for a period of time, to the target site of the subject, wherein the alternating electric field releases the therapeutic from lipid capsule at the target site of the subject.

Disclosed are methods of increasing target site specific release of a therapeutic agent in a subject comprising administering a lipid capsule to a target site of a subject, wherein the lipid capsule comprises a therapeutic agent; and applying an alternating electric field, at a frequency for a period of time, to the target site of the subject, wherein the alternating electric field releases the therapeutic agent from the lipid capsule at the target site of the subject, thereby increasing the target site specific release of the therapeutic agent.

Disclosed are methods of treating comprise administering a lipid capsule to a target site of a subject in need thereof, wherein the lipid capsule comprises a therapeutic agent; and applying an alternating electric field, at a frequency for a period of time, to the target site of the subject in need thereof, wherein the alternating electric field releases the therapeutic agent from the lipid capsule at the target site of the subject in need thereof.

Disclosed are methods of killing a cell comprising administering a lipid capsule to a target site, wherein the lipid capsule comprises a therapeutic agent; and applying an alternating electric field for a period of time, to the target site, wherein the alternating electric field releases the therapeutic agent from the v at the target site, wherein the target site comprises a cell, wherein the therapeutic kills the cell.

Disclosed are drug delivery systems comprising a lipid capsule comprising a therapeutic agent; and a device capable of administering an alternating electric field.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

DETAILED DESCRIPTION

The disclosed method and compositions may be understood more readily by reference to the following detailed description of particular embodiments and the Example included therein and to the Figures and their previous and following description.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Definitions

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. In some aspects, for example, reference to "a lipid capsule" includes a plurality of such lipid capsules, reference to "the lipid capsule" is a reference to one or more lipid capsules and equivalents thereof known to those skilled in the art, and so forth.

As used herein, a "target site" is a specific site or location within or present on a subject or patient. For example, a "target site" can refer to, but is not limited to a cell (e.g. a cancer cell), population of cells, organ, tissue, or a tumor. In some aspects, the phrase "target cell" can be used to refer to target site, wherein the target site is or comprises a cell. In some aspects, organs that can be target sites include, but are not limited to, lung, brain, pancreas, abdominal organs (e.g. stomach, intestine), ovary, breast, uterus, prostate, bladder, liver, colon, or kidney. In some aspects, a target site can be a fibrotic tissue or lymph node. In some aspects, a cell or population of cells that can be a target site include, but are not limited to, lung cells, brain cells, pancreatic cells, abdominal cells, ovarian cells, liver cells, colon cells, or kidney cells. In some aspects, a "target site" can be a tumor target site. In some aspects, a "target site" can be a virus-infected cell. In some aspects, a "target cell" can be a cancer. In some aspects, a "target cell" can be a virus-infected cell.

A "tumor target site" is a site or location within or present on a subject or patient that comprises or is adjacent to one or more cancer cells, previously comprised one or more tumor cells, or is suspected of comprising one or more tumor cells. For example, a tumor target site can refer to a site or location within or present on a subject or patient that is prone to metastases. Additionally, a target site or tumor target site can refer to a site or location of a resection of a primary tumor within or present on a subject or patient. Additionally, a target site or tumor target site can refer to a site or location adjacent to a resection of a primary tumor within or present on a subject or patient.

As used herein, an "alternating electric field" or "alternating electric fields" refers to a very-low-intensity, directional, intermediate-frequency alternating electrical fields delivered to a subject, a sample obtained from a subject or to a specific location within a subject or patient (e.g. a target site such as a cell). In some aspects, the alternating electrical fields can be in a single direction or multiple directional. In some aspects, alternating electric fields can be delivered through two pairs of transducer arrays that generate perpendicular fields within the target site. For example, for the Optune™ system (an alternating electric fields delivery system) one pair of electrodes is located to the left and right (LR) of the target site, and the other pair of electrodes is located anterior and posterior (AP) to the target site. Cycling the field between these two directions (i.e., LR and AP) ensures that a maximal range of cell orientations is targeted.

As used herein, an "alternating electric field" applied to a tumor target site can be referred to as a "tumor treating fields" or "TTFields." TTFields have been established as an anti-mitotic cancer treatment modality because they interfere with proper micro-tubule assembly during metaphase and eventually destroy the cells during telophase, cytokinesis, or subsequent interphase. TTFields target solid tumors and are described in U.S. Pat. No. 7,565,205, which is incorporated herein by reference in its entirety for its teaching of TTFields In-vivo and in-vitro studies show that the efficacy of TTFields therapy increases as the intensity of the electrical field increases. Therefore, optimizing array placement on a subject to increase the intensity in the target site or target cell is standard practice for the Optune system. Array placement optimization may be performed by "rule of thumb" (e.g., placing the arrays on the subject as close to the target site or target cell as possible), measurements describing the geometry of the patient's body, target site dimensions, and/or target site or cell location. Measurements used as input may be derived from imaging data. Imaging data is intended to include any type of visual data, such as for example, single-photon emission computed tomography (SPECT) image data, x-ray computed tomography (x-ray CT) data, magnetic resonance imaging (MRI) data, positron emission tomography (PET) data, data that can be captured by an optical instrument (e.g., a photographic camera, a charge-coupled device (CCD) camera, an infrared camera, etc.), and the like. In certain implementations, image data may include 3D data obtained from or generated by a 3D scanner (e.g., point cloud data). Optimization can rely on an understanding of how the electrical field distributes within the target site or target cell as a function of the positions of the array and, in some aspects, take account for variations in the electrical property distributions within the heads of different patients.

The term "subject" refers to the target of administration, e.g. an animal. Thus, the subject of the disclosed methods can be a vertebrate, such as a mammal. For example, the subject can be a human. The term does not denote a particular age or sex. A subject can be used interchangeably with "individual" or "patient." For example, the subject of administration or exposure to can mean the recipient of the alternating electrical fields.

By "treat" is meant to administer or apply a therapeutic, such as alternating electric fields and a vector, to a subject, such as a human or other mammal (for example, an animal model), that has an infection (e.g. viral) or disease (e.g. cancer) or has an increased susceptibility for developing an infection or disease, in order to prevent or delay a worsening of the effects of the disease or infection, or to partially or fully reverse the effects of the infection or disease. For example, treating a subject having cancer can comprise delivering a therapeutic to a cell in the subject.

By "prevent" is meant to minimize or decrease the chance that a subject develops an infection or disease.

As used herein, the terms "administering" and "administration" refer to any method of providing a therapeutic, such as an antiviral agent or anti-cancer therapeutic, to a target site or subject. Such methods are well known to those skilled in the art and include, but are not limited to: oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition. In an aspect, the skilled person can determine an efficacious dose, an efficacious schedule, or an efficacious route of administration so as to treat a subject. In some aspects, administering comprises exposing or applying. In some aspects, exposing a target site or subject to alternating electrical fields or applying alternating electrical fields to a target site or subject means administering alternating electrical fields to the target site or subject.

As used herein, a "therapeutically effective amount" is an amount of a composition (e.g. lipid capsule comprising a therapeutic agent), that provides a therapeutic benefit to an individual or subject. For example, a therapeutically effective amount of a lipid capsule comprising a therapeutic agent is an amount that treats, alleviates, ameliorates, relieves, alleviates symptoms of, prevents, delays onset of, inhibits progression of, reduces severity of, and/or reduces incidence of a disease or infection. In one embodiment, a therapeutically effective amount of a lipid capsule comprising a therapeutic agent will result in an improvement to, or prevents or slows the worsening of, one or more indicators or symptoms of an infection or disease, such as those described herein. As used herein, "treating" a subject with cancer includes administering a therapeutically effective amount of a composition disclosed herein.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

B. Compositions

Disclosed are lipid capsules comprising a therapeutic agent. Disclosed are lipid capsules that can be loaded with a compound or drug of interest. In some aspects, disclosed are drug-loaded lipid capsules. In some aspects, the term "drug" can be used to mean a chemical compound, a peptide, a nucleic acid sequence, or an antibody. In some aspects, the term "drug" refers to a therapeutic agent.

In some aspects, the lipid capsules comprises an outer surface, wherein the outer surface comprises a lipid layer. In some aspects, the lipid layer is a lipid bilayer. In some aspects, the lipid capsule comprises phospholipids. For example, the lipid bilayer can comprise phospholipids.

In some aspects, lipid capsules comprise dipole moment bearing molecules. The presence of the dipole moment bearing molecules allow for dipole moments, which occur when there is a separation of charge. Dipole moments can occur between two ions in an ionic bond or between atoms in a covalent bond; dipole moments can arise from differences in electronegativity. The larger the difference in electronegativity, the larger the dipole moment. Phospholipids are the building blocks of most biocompatible drug delivery systems. Phospholipids are usually structured in a bilayer since they have a hydrophilic "head" and a hydrophobic "tail". This structure resembles a eukaryotic cell membrane. The dipole moment and cellular structure with a hydrophobic core and hydrophilic outer surface is affected by alternating electrical fields and causes an increased permeability of the membrane.

In some aspects, the lipid capsule comprises an outer surface, wherein the outer surface comprises a lipid layer. In some aspects, the lipid layer is a lipid bilayer. In some aspects, the lipid capsule comprises phospholipids. In some aspects, the lipid capsule comprises a polyethylene glycol (PEG) coating. In some aspects, a lipid capsule is identified as comprising a lipid core shell nanostructure. In some aspects, a lipid capsule is composed of an external shell, formed of solid lipids and emulsifying agents, and an oily core, wherein the therapeutic agent is present in the oily core. In some aspects, a lipid capsule comprises a liquid based core, wherein the liquid based core is saline based. For example, the lipid capsule can comprise an ethanol core and external salt solution.

In some aspects, the lipid capsule is 5-500 nm. In some aspects, the lipid capsule is 50-400 nm. In some aspects, the lipid capsule is 50-150 nm. In some aspects, the lipid capsule is 100-300 nm.

In some aspects, the lipid capsules are sub-micron colloidal carriers ranging from 50 to 1000 nm, made up of physiological lipid dispersed in water or aqueous surfactant solution.

In some aspects, the lipid capsules are solid lipid nanoparticles or nanostructured lipid carriers. Solid lipid nanoparticles combine advantages such as physical stability, protection of incorporated labile drugs, controlled release and excellent tolerability of other innovative carrier system (fat emulsion, liposomes and polymeric nanoparticles) while at the same time minimizing the associated problem. Solid lipid nanoparticle can be produced on large industrial scale by high pressure homogenization. The solid matrix of solid lipid nanoparticle can protect the active ingredient which is incorporated into it and protects from chemical degradation which ultimately increases the drug release profile. The different formulations of solid lipid nanoparticle have developed for various application routes (parenteral, oral, dermal, ocular, pulmonary, and rectal). Solid lipid nanoparticles are especially useful in ocular drug delivery as they can enhance the corneal absorption of drugs and improve the ocular bioavailability of both hydrophilic and lipophilic drugs. Solid lipid nanoparticles are composed of 0.1% (w/w) to 30% (w/w) solid lipid dispersed in an aqueous medium and if necessary stabilized with preferably 0.5% (w/w) to 5% (w/w) surfactant.

Examples of lipid capsules that can be used in the compositions and methods described herein as well as how they can be made can include, but are not limited to the lipid capsules described in U.S. Pat. No. 5,250,236; EP 0605497, U.S. Patent Application No. 20080311214A1, U.S. Pat. No. 7,147,841 B2; U.S. Pat. No. 11,921,634; EP1838286 B1, EP2413918 A1, EP2549977 A2, and U.S. Pat. No. 5,785,976.

In some aspects, the drug (therapeutic agent) in the drug-loaded lipid capsules can be, but is not limited to, an anti-cancer drug or cancer therapeutic. In some aspects, the anti-cancer drug can be, but is not limited to, alkylating agents, antimetabolites, natural products, hormones, as well as a variety of other chemicals that do not fall within these discrete classes but are capable of preventing the replication of cancer cells or killing cancer cells. For example, the drug can be, but is not limited to, doxorubicin, Gemcitabine (GEM), abraxane, erlotinib, or everolimus. In some aspects, the drug can be any therapeutic agent.

In some aspects, the drug in the drug-loaded lipid capsules can be, but is not limited to, a lipid capsule comprising an anti-viral, anti-fungal, anti-bacterial, or any pathogen specific drug.

In some aspects, the drug in the drug-loaded lipid capsules can be, but is not limited to, a lipid capsule comprising a pro-inflammatory molecule or an anti-inflammatory molecule.

1. Pharmaceutical Compositions and Delivery

Disclosed herein are pharmaceutical compositions comprising one or more of the lipid capsules described herein. In some aspects, the lipid capsules described herein can be provided in a pharmaceutical composition. For example, the lipid capsules described herein can be formulated with a pharmaceutically acceptable carrier.

In some aspects, a pharmaceutical composition can comprise a therapeutic agent. In some aspects, a pharmaceutical composition can comprise a therapeutic agent and one or more of the lipid capsules described herein. For example, disclosed herein are pharmaceutical compositions comprising one or more of the lipid capsules described herein and a therapeutic such as an anti-cancer drug. In particular, disclosed herein are pharmaceutical compositions comprising one or more of the lipid capsules disclosed herein wherein the lipid capsules are drug-loaded lipid capsules. In some aspects, the drug can be an anti-cancer drug. In some aspects, the anti-cancer drug can be a chemotherapeutic. In some aspects, the chemotherapeutic can be, but is not limited to, an anticancer drug, a cytotoxic drug, pain-management drug, pseudomonas exotoxin A, a non-radioactive isotope (e.g. boron-10 for boron neutron capture therapy), and/or a photosensitizer (e.g. photofrin, foscan, 5-aminolevulinic acid, Mono-L-aspartyl chlorine, pthalocyanines, Meta-tetra(hydroxyphenyl)porphyrins, texaphyrins, Tin ethyl etipurpurin). In some aspects, a chemotherapeutic agent can be, but is not limited to, an alkylating agent, an antimetabolite agent, an antineoplastic antibiotic agent, a mitotic inhibitor agent, a checkpoint inhibitor, and a kinase inhibitor. In some aspects, the drug in the drug-loaded lipid capsules can be, but is not limited to, a lipid capsule comprising an anti-viral, anti-fungal, anti-bacterial, or any pathogen specific drug. In some aspects, the drug in the drug-loaded lipid capsules can be, but is not limited to, a lipid capsule comprising a pro-inflammatory molecule or an anti-inflammatory molecule.

Any of the therapeutic agents listed above as examples of a sequence of interest can also be provided separate from the vector as part of the pharmaceutical composition.

Disclosed herein are compositions comprising one or more of the lipid capsules described herein that further comprise a carrier such as a pharmaceutically acceptable carrier. For example, disclosed are pharmaceutical compositions, comprising the lipid capsules disclosed herein, and a pharmaceutically acceptable carrier.

For example, pharmaceutical compositions comprising the lipid capsules described herein can comprise a pharmaceutically acceptable carrier. By "pharmaceutically acceptable" is meant a material or carrier that would be selected to minimize any degradation of the active ingredient and to minimize any adverse side effects in the subject, as would be well known to one of skill in the art. Examples of carriers include dimyristoylphosphatidyl (DMPC), phosphate buffered saline or a multivesicular liposome. For example, PG:PC:Cholesterol:peptide or PC:peptide can be used as carriers in this invention. Other suitable pharmaceutically acceptable carriers and their formulations are described in Remington: The Science and Practice of Pharmacy (19th ed.) ed. A. R. Gennaro, Mack Publishing Company, Easton, PA 1995. Typically, an appropriate amount of pharmaceutically-acceptable salt is used in the formulation to render the formulation isotonic. Other examples of the pharmaceutically-acceptable carrier include, but are not limited to, saline, Ringer's solution and dextrose solution. The pH of the solution can be from about 5 to about 8, or from about 7 to about 7.5. Further carriers include sustained release preparations such as semi-permeable matrices of solid hydrophobic polymers containing the composition, which matrices are in the form of shaped articles, e.g., films, stents (which are implanted in vessels during an angioplasty procedure), liposomes or microparticles. It will be apparent to those persons skilled in the art that certain carriers may be more preferable depending upon, for instance, the route of administration and concentration of vector being administered. These most typically would be standard carriers for administration of drugs to humans, including solutions such as sterile water, saline, and buffered solutions at physiological pH.

Pharmaceutical compositions can also include carriers, thickeners, diluents, buffers, preservatives and the like, as long as the intended activity of the polypeptide, peptide, nucleic acid, vector of the invention is not compromised. Pharmaceutical compositions may also include one or more active ingredients (in addition to the composition of the invention) such as antimicrobial agents, anti-inflammatory agents, anesthetics, and the like. The pharmaceutical composition may be administered in a number of ways depending on whether local or systemic treatment is desired, and on the area to be treated.

Preparations of parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for optical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids, or binders may be desirable. Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mon-, di-, trialkyl and aryl amines and substituted ethanolamines.

In the methods described herein, delivery (or administration or introduction) of the vector or pharmaceutical compositions disclosed herein to subjects can be via a variety of mechanisms.

Disclosed are methods comprising introducing a lipid capsule to a cell. In some aspects, the methods comprising introducing a lipid capsule to a target site. In some aspects the methods comprise introducing a lipid capsule to a subject. In some aspects, a subject comprises a cell that is the target site for the disclosed lipid capsule. In some aspects, all of the disclosed methods comprising introducing a lipid capsule to a cell also comprise introducing a lipid capsule to a subject.

C. Alternating Electric Fields

The methods disclosed herein comprise alternating electric fields. In some aspects, the alternating electric fields used in the methods disclosed herein is a tumor-treating field. In some aspects, the alternating electric fields can vary dependent on the type of cell or condition to which the alternating electric fields are applied. In some aspects, the alternating electric field can be applied through one or more electrodes placed on the subject's body. In some aspects, there can be two or more pairs of electrodes. For example, arrays can be placed on the front/back and sides of a patient and can be used with the systems and methods disclosed herein. In some aspects, where two pairs of electrodes are used, the alternating electric field can alternate between the pairs of electrodes. For example, a first pair of electrodes can be placed on the front and back of the subject and a second pair of electrodes can be placed on either side of the subject, the alternating electric field can then be applied and can alternate between the front and back electrodes and then to the side to side electrodes.

In some aspects, the frequency of the alternating electric fields is between 100 and 500 kHz. The frequency of the alternating electric fields can also be, but is not limited to, between 50 and 500 kHz, between 100 and 500 kHz, between 25 kHz and 1 MHz, between 50 and 190 kHz, between 25 and 190 kHz, between 180 and 220 kHz, or between 210 and 400 kHz. In some aspects, the frequency of the alternating electric fields can be electric fields at 50 kHz, 100 kHz, 150 kHz, 200 kHz, 250 kHz, 300 kHz, 350 kHz, 400 kHz, 450 kHz, 500 kHz, or any frequency between. In some aspects, the frequency of the alternating electric fields is from about 200 kHz to about 400 kHz, from about 250 kHz to about 350 kHz, and may be around 300 kHz.

In some aspects, the field strength of the alternating electric fields can be between 1 and 4 V/cm RMS. In some aspects, different field strengths can be used (e.g., between 0.1 and 10 V/cm). In some aspects, the field strength can be 1.75 V/cm RMS. In some embodiments the field strength is at least 1 V/cm RMS. In other embodiments, combinations of field strengths are applied, for example combining two or more frequencies at the same time, and/or applying two or more frequencies at different times.

In some aspects, the alternating electric fields can be applied for a variety of different intervals ranging from 0.5 hours to 72 hours. In some aspects, a different duration can be used (e.g., between 0.5 hours and 14 days). In some aspects, application of the alternating electric fields can be repeated periodically. For example, the alternating electric fields can be applied every day for a two-hour duration.

In some aspects, the exposure may last for at least 6 hours, at least 12 hours, at least 24 hours, at least 36 hours, at least 48 hours, or at least 72 hours or more.

The disclosed methods comprising applying one or more alternating electric fields to a cell or to a subject. In some aspects, the alternating electric fields are applied to a target site or tumor target site. When applying alternating electric fields to a cell, this can often refer to applying alternating electric fields to a subject comprising a cell. In some aspects, applying alternating electric fields to a target site of a subject results in applying alternating electric fields to a cell.

D. Methods of Delivering a Therapeutic to a Target Site

Disclosed are methods of delivering a therapeutic to a target site of a subject comprising administering a lipid capsule to a target site of a subject, wherein the lipid capsule comprises a therapeutic agent; and applying alternating electric fields, at a frequency for a period of time, to the target site of the subject, wherein the alternating electric fields release the therapeutic from lipid capsule at the target site of the subject. In some aspects, alternating electric fields can increase the permeability of the lipids in the outer surface of a lipid capsule. The increased permeability thus allows the therapeutic agent inside the lipid capsule to be able to leak out. Phospholipids are the building blocks of most biocompatible drug delivery systems. Phospholipids are usually structured in a bilayer since they have a hydrophilic "head" and a hydrophobic "tail". This structure resembles a eukaryotic cell membrane. The dipole moment and cellular structure with a hydrophobic core and hydrophilic outer surface is affected by alternating electrical fields and causes an increased permeability of the membrane. As such, the lipid capsules that reach target sites (e.g. tumor or inflammation site) will be disrupted as a result of enhance permeability and retention effect (EPR) in response to alternating electrical fields.

In some aspects, the lipid capsule is loaded with a therapeutic agent. In some aspects, the therapeutic agent is encapsulated in the nanoparticle. In some aspects, the lipid capsules can be actively or passively loaded with a therapeutic agent. In some aspects, the lipid capsule is coated with a therapeutic agent. In some aspects, the therapeutic agent is conjugated to the lipid capsule. For example, the conjugation can be via a linker. In some aspects, the linker can be cleavable. There are several ways a lipid capsule can "carry" a therapeutic agent, all of which are considered herein.

In some aspects, the therapeutic agent can be a small molecule, nucleic acid, carbohydrate, lipid, peptide, antibody, or antibody fragment. In some aspects, the therapeutic agent can be any composition capable of treating a disease of interest. For example, a therapeutic agent can be, but is not limited to, an anti-cancer therapeutic, an anti-viral therapeutic, an anti-bacterial therapeutic, an anti-fungal therapeutic, a pro-inflammatory therapeutic, or an anti-inflammatory therapeutic. In some aspects, an anti-cancer therapeutic can be Gemcitabine (GEM), paclitaxel, doxorubicin, cytarabine, daunorubicin, or any chemotherapeutic. In some aspects, a therapeutic agent can be a nucleic acid, siRNA, an antisense oligonucleotide, or an aptamer.

In some aspects, the lipid capsule comprises a cell-specific targeting moiety. In some aspects, the cell-specific targeting moiety can be a cancer cell-specific targeting moiety.

In some aspects, the targeting moiety can direct, or target, the lipid capsule to a specific cell. The cell-specific targeting moiety can be a chemical, compound, peptide or nucleic acid. Examples of targeting moieties include, but art not limited to, molecules that recognize receptors on specific cell types.

In some aspects, the lipid capsule can comprise a cell penetrating peptide. In some aspects, a cell penetrating peptide can facilitate the delivery of the lipid capsule to the cytoplasm of the cell.

In some aspects, the lipid capsule is labeled. As used herein, a label, or detection agent, is any molecule that can be associated with a lipid capsule, directly or indirectly, and which results in a measurable, detectable signal, either directly or indirectly. Many such labels for incorporation into lipid capsule or coupling to lipid capsule are known to those of skill in the art. Examples of detection agents can be, but are not limited to, radioactive isotopes, fluorescent molecules, phosphorescent molecules, enzymes, antibodies, and ligands.

Examples of suitable fluorescent labels include fluorescein (FITC), 5,6-carboxymethyl fluorescein, Texas red, nitrobenz-2-oxa-1,3-diazol-4-yl (NBD), coumarin, dansyl chloride, rhodamine, 4'-6-diamidino-2-phenylinodole (DAPI), and the cyanine dyes Cy3, Cy3.5, Cy5, Cy5.5 and Cy7. Preferred fluorescent labels are fluorescein (5-carboxyfluorescein-N-hydroxysuccinimide ester) and rhodamine (5,6-tetramethyl rhodamine). Preferred fluorescent labels for combinatorial multicolor coding are FITC and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. The fluorescent labels can be obtained from a variety of commercial sources, including Molecular Probes, Eugene, OR and Research Organics, Cleveland, Ohio.

In some instances, a label can be, but is not limited to, an isotope marker, colorimetric biosensors, or fluorescent labels. For example, fluorescent markers can be, but are not limited to, green fluorescent protein (GFP) or rhodamine fluorescent protein (RFP). Other labels can include biotin, streptavidin, horseradish peroxidase, or luciferase.

In some aspects, the target site comprises a cell. For example, the cell can be, but is not limited to, a cancer cell, a pathogen-infected cell, or an immune cell. In some aspects, a cancer cell can be, but is not limited to, a pancreatic cancer cell, glioblastoma cell or lung metastatic carcinoma cell. In some aspects, a pathogen-infected cell can be a virus infected, bacteria infected, or fungus infected cell. In some aspects, the lipid capsule enters the target site. For example, in some aspects, target site is a cancer cell or pathogen-infected cell and the lipid capsule can enter the cancer cell or pathogen-infected cell. In some aspects, the target site is the lungs and the lipid capsule can enter the lungs.

In some aspects, the subject has cancer, an infection, an inflammatory disorder, or is immune suppressed. In some aspects, the therapeutic is an anti-cancer, anti-infectious agent, anti-inflammatory or pro-inflammatory therapeutic.

In some aspects, the frequency of the alternating electric field is between 100 and 500 kHz. In some aspects, the frequency of the alternating electric field is between 180 and 220 kHz. In some aspects, the frequency of the alternating electric field is between 50 and 500 kHz or 50 and 1 MHz.

Also disclosed are methods of delivering a therapeutic to a target site of a subject comprising administering a lipid capsule to a target site of a subject, wherein the lipid capsule comprises a therapeutic agent; and applying an alternating electric field, at a frequency for a period of time, to the target site of the subject, wherein the alternating electric field releases the therapeutic from the lipid capsule at the target site of the subject, and further comprising applying a second alternating electric fields at a second frequency to the target site prior to, during or after the step of administering the lipid capsule to the target site of the subject. In some aspects, disclosed are methods that allow the lipid capsule to get to a target site and the alternating electric fields cause the lipid capsule to increase permeability thus releasing the therapeutic from the lipid capsule near a cell but not within the cell. Also disclosed are methods that allow the lipid capsule to get to a target site and a first alternating electric fields causes the lipid capsule to enter a cell and a second alternating electric field causes the lipid capsule to increase permeability thus releasing the therapeutic from the lipid capsule within the cell. In some aspects, the second alternating electric fields increase permeability of a cell membrane of a cell at the target site of the subject.

In some aspects, the lipid capsule enters a cell, such as a cancer cell or pathogen-infected cell, prior to releasing the therapeutic.

In some aspects, when a second alternating electric fields are applied, the first and second alternating electric fields can be at the same frequency or at different frequencies. In some aspects, the first and second alternating electric fields can be at different lengths of time for the same lengths of time.

In some aspects, the lipid capsule is administered prior to exposing the target site to the alternating electric field. In some aspects, the lipid capsule is administered at the same time as (or during) the alternating electric fields. In some aspects, the lipid capsule is administered after the alternating electric fields.

E. Methods of Increasing Target Site Specific Release of a Drug

Disclosed are methods of increasing target site specific release of a therapeutic agent in a subject comprising administering a lipid capsule to a target site of a subject, wherein the lipid capsule comprises a therapeutic agent; and applying alternating electric fields, at a frequency for a period of time, to the target site of the subject, wherein the alternating electric fields release the therapeutic agent from the lipid capsule at the target site of the subject, thereby increasing the target site specific release of the therapeutic agent.

In some aspects, an increase in the target site specific release of the therapeutic agent can be determined by comparing the release of the therapeutic agent at the target site in the presence and absence of alternating electric fields. An increase in the target site specific release of the therapeutic agent can be detected in the presence of alternating electric fields compared to in the absence of alternating electric fields.

In some aspects, the lipid capsule is loaded with a therapeutic agent. In some aspects, the therapeutic agent is encapsulated in the lipid capsule. In some aspects, the lipid capsules can be actively or passively loaded with a therapeutic agent. In some aspects, the lipid capsule is coated with a therapeutic agent. In some aspects, the therapeutic agent is conjugated to the lipid capsule. For example, the conjugation can be via a linker. In some aspects, the linker can be cleavable. There are several ways a lipid capsule can "carry" a therapeutic agent, all of which are considered herein.

In some aspects, the therapeutic agent can be a small molecule, nucleic acid, carbohydrate, lipid, peptide, antibody, or antibody fragment. In some aspects, the therapeutic agent can be any composition capable of treating a disease of interest. For example, a therapeutic agent can be, but is not limited to, an anti-cancer therapeutic, an anti-viral therapeutic, an anti-bacterial therapeutic, an anti-fungal therapeutic, a pro-inflammatory therapeutic, or an anti-inflammatory therapeutic. In some aspects, an anti-cancer therapeutic can be Gemcitabine (GEM), paclitaxel, doxorubicin, cytarabine, daunorubicin, or any chemotherapeutic. In some aspects, a therapeutic agent can be a siRNA, antisense oligonucleotide, or aptamers.

In some aspects, the lipid capsule can comprise a cell-specific targeting moiety. In some aspects, the cell-specific targeting moiety can be a cancer cell-specific targeting moiety.

In some aspects, the targeting moiety can direct, or target, the lipid capsule to a specific cell or group of cells. The cell-specific targeting moiety can be a chemical, compound, peptide or nucleic acid. Examples of targeting moieties include, but art not limited to, molecules that recognize receptors on specific cell types.

In some aspects, the lipid capsule can comprise a cell penetrating peptide. In some aspects, a cell penetrating peptide can facilitate the delivery of the lipid capsule to the cytoplasm of the cell.

In some aspects, the lipid capsule is labeled. As used herein, a label, or detection agent, is any molecule that can be associated with a lipid capsule, directly or indirectly, and which results in a measurable, detectable signal, either directly or indirectly. Many such labels for incorporation into lipid capsule or coupling to lipid capsule are known to those of skill in the art. Examples of detection agents can be, but are not limited to, radioactive isotopes, fluorescent molecules, phosphorescent molecules, enzymes, antibodies, and ligands.

Examples of suitable fluorescent labels include fluorescein (FITC), 5,6-carboxymethyl fluorescein, Texas red, nitrobenz-2-oxa-1,3-diazol-4-yl (NBD), coumarin, dansyl chloride, rhodamine, 4'-6-diamidino-2-phenylinodole (DAPI), and the cyanine dyes Cy3, Cy3.5, Cy5, Cy5.5 and Cy7. Preferred fluorescent labels are fluorescein (5-carboxyfluorescein-N-hydroxysuccinimide ester) and rhodamine (5,6-tetramethyl rhodamine). Preferred fluorescent labels for combinatorial multicolor coding are FITC and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. The fluorescent labels can be obtained from a variety of commercial sources, including Molecular Probes, Eugene, OR and Research Organics, Cleveland, Ohio.

In some instances, a label can be, but is not limited to, an isotope marker, colorimetric biosensors, or fluorescent labels. For example, fluorescent markers can be, but are not limited to, green fluorescent protein (GFP) or rhodamine fluorescent protein (RFP). Other labels can include biotin, streptavidin, horseradish peroxidase, or luciferase.

In some aspects, the lipid capsule comprises an outer surface, wherein the outer surface comprises a lipid layer. In some aspects, the lipid layer is a lipid bilayer. In some aspects, the lipid capsule comprises phospholipids. In some aspects, the lipid capsule comprises a polyethylene glycol (PEG) coating. In some aspects, a lipid capsule is identified as comprising a lipid core shell nanostructure. In some aspects, a lipid capsule is composed of an external shell, formed of solid lipids and emulsifying agents, and an oily core, wherein the therapeutic agent is present in the oily core. In some aspects, a lipid capsule comprises a liquid based core, wherein the liquid based core is saline based. For example, the lipid capsule can comprise an ethanol core and external salt solution.

In some aspects, the lipid capsule is 5-500 nm. In some aspects, the nanoparticle is 50-400 nm. In some aspects, the nanoparticle is 50-150 nm. In some aspects, the nanoparticle is 100-300 nm.

In some aspects, the target site comprises a cell. For example, the cell can be, but is not limited to, a cancer cell, a pathogen-infected cell, or an immune cell. In some aspects, a cancer cell can be, but is not limited to, a pancreatic cancer cell, glioblastoma cell or lung metastatic carcinoma cell. In some aspects, a pathogen-infected cell can be a virus infected, bacteria infected, or fungus infected cell. In some aspects, the lipid capsule enters the target site. For example, in some aspects, target site is a cancer cell or pathogen-infected cell and the lipid capsule can enter the cancer cell or pathogen-infected cell. In some aspects, the target site is the lungs and the lipid capsule can enter the lungs.

In some aspects, the subject has cancer, an infection, an inflammatory disorder, or is immune suppressed. In some aspects, the therapeutic is an anti-cancer, anti-infectious agent, anti-inflammatory or pro-inflammatory therapeutic.

In some aspects, the frequency of the alternating electric field is between 100 and 500 kHz. In some aspects, the frequency of the alternating electric field is between 180 and 220 kHz. In some aspects, the frequency of the alternating electric field is between 50 and 500 kHz or 50 and 1 MHz.

Also disclosed are methods of increasing target site specific release of a therapeutic to a target site of a subject comprising administering a lipid capsule to a target site of a subject, wherein the lipid capsule comprises a therapeutic agent; and applying alternating electric fields, at a frequency for a period of time, to the target site of the subject, wherein the alternating electric fields release the therapeutic from lipid capsule at the target site of the subject, thereby increasing the target site specific release of the therapeutic agent and further comprising applying a second alternating electric fields at a second frequency to the target site prior to, during or after the step of administering the lipid capsule to the target site of the subject. In some aspects, disclosed are methods that allow the lipid capsule to get to a target site and the alternating electric fields cause the lipid capsule to increase permeability thus releasing the therapeutic from the lipid capsule near a cell but not within the cell. Also disclosed are methods that allow the lipid capsule to get to a target site and a first alternating electric field causes the lipid capsule to enter a cell and a second alternating electric field causes the lipid capsule to increase permeability, thereby releasing the therapeutic from the lipid capsule within the cell. In some aspects, the second alternating electric field increases permeability of a cell membrane of a cell at the target site of the subject.

In some aspects, when a second alternating electric fields are applied, the first and second alternating electric fields can be at the same frequency or at different frequencies. In some aspects, the first and second alternating electric fields can be at different lengths of time for the same lengths of time.

In some aspects, the lipid capsule is administered prior to exposing the target site to the alternating electric fields. In some aspects, the lipid capsule is administered at the same time as the alternating electric fields. In some aspects, the lipid capsule is administered after the alternating electric fields.

F. Methods of Treating

Disclosed are methods of treating a subject in need thereof, wherein the subject in need thereof has cancer, has an infection, has an inflammatory disorder, or is immune suppressed. In some aspects, the methods of treating comprise administering a lipid capsule to a target site of a subject in need thereof, wherein the lipid capsule comprises a therapeutic agent; and applying alternating electric fields, at a frequency for a period of time, to the target site of the subject in need thereof, wherein the alternating electric fields release the therapeutic agent from the lipid capsule at the target site of the subject in need thereof. Once released, the drug can provide a therapeutic effect. In some aspects, the therapeutic effect is to kill the cell (such as a cancer cell or a pathogen infected cell), reduce inflammation, or increase the humoral and/or cell-mediated immune response.

In some aspects, the subject has cancer, an infection, an inflammatory disorder, or is immune suppressed. In some aspects, the subject has a neurodegenerative disease, auto-immune disease, or orthopedic condition. In some aspects, the infection can be a viral, bacterial or fungal infection. In some aspects, the cancer can be brain cancer, pancreatic cancer, lung cancer, ovarian cancer, or breast cancer. In some aspects, the therapeutic is an anti-cancer, anti-infectious agent, anti-inflammatory or pro-inflammatory therapeutic.

Disclosed are methods of treating cancer in a subject comprising administering a lipid capsule to a target site of a subject having cancer, wherein the lipid capsule comprises a therapeutic agent; and applying alternating electric fields, at a frequency for a period of time, to the target site of the subject having cancer, wherein the target site comprises a cancer cell; wherein the alternating electric fields release the therapeutic agent from the lipid capsule at the target site of the subject; wherein the therapeutic kills the cancer cell.

In some aspects, the lipid capsule is loaded with a therapeutic agent. In some aspects, the therapeutic agent is encapsulated in the lipid capsule. In some aspects, the lipid capsules can be actively or passively loaded with a therapeutic agent. In some aspects, the lipid capsule is coated with a therapeutic agent. In some aspects, the therapeutic agent is conjugated to the lipid capsule. For example, the conjugation can be via a linker. In some aspects, the linker can be cleavable. There are several ways a lipid capsule can "carry" a therapeutic agent, all of which are considered herein.

In some aspects, the therapeutic agent can be a small molecule, nucleic acid, carbohydrate, lipid, peptide, antibody, or antibody fragment. In some aspects, the therapeutic agent can be any composition capable of treating a disease of interest. For example, a therapeutic agent can be, but is not limited to, an anti-cancer therapeutic, an anti-viral therapeutic, an anti-bacterial therapeutic, an anti-fungal therapeutic, a pro-inflammatory therapeutic, or an anti-inflammatory therapeutic. In some aspects, an anti-cancer therapeutic can be Gemcitabine (GEM), paclitaxel, doxorubicin, cytarabine, daunorubicin, or any chemotherapeutic. In some aspects, a therapeutic agent can be a siRNA, antisense oligonucleotide, or aptamers.

In some aspects, the lipid capsule comprises a cell-specific targeting moiety. In some aspects, the cell-specific targeting moiety can be a cancer cell-specific targeting moiety.

In some aspects, the targeting moiety can direct, or target, the lipid capsule to a specific cell. The cell-specific targeting moiety can be a chemical, compound, peptide or nucleic acid. Examples of targeting moieties include, but art not limited to, molecules that recognize receptors on specific cell types.

In some aspects, the lipid capsule can comprise a cell penetrating peptide. In some aspects, a cell penetrating peptide can facilitate the delivery of the lipid capsule to the cytoplasm of the cell.

In some aspects, the lipid capsule is labeled. As used herein, a label, or detection agent, is any molecule that can be associated with a lipid capsule, directly or indirectly, and which results in a measurable, detectable signal, either directly or indirectly. Many such labels for incorporation into lipid capsules or coupling to nanoparticles are known to those of skill in the art. Examples of detection agents can be, but are not limited to, radioactive isotopes, fluorescent molecules, phosphorescent molecules, enzymes, antibodies, and ligands.

Examples of suitable fluorescent labels include fluorescein (FITC), 5,6-carboxymethyl fluorescein, Texas red, nitrobenz-2-oxa-1,3-diazol-4-yl (NBD), coumarin, dansyl chloride, rhodamine, 4'-6-diamidino-2-phenylinodole (DAPI), and the cyanine dyes Cy3, Cy3.5, Cy5, Cy5.5 and Cy7. Preferred fluorescent labels are fluorescein (5-carboxyfluorescein-N-hydroxysuccinimide ester) and rhodamine (5,6-tetramethyl rhodamine). Preferred fluorescent labels for combinatorial multicolor coding are FITC and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. The fluorescent labels can be obtained from a variety of commercial sources, including Molecular Probes, Eugene, OR and Research Organics, Cleveland, Ohio.

In some instances, a label can be, but is not limited to, an isotope marker, colorimetric biosensors, or fluorescent labels. For example, fluorescent markers can be, but are not limited to, green fluorescent protein (GFP) or rhodamine fluorescent protein (RFP). Other labels can include biotin, streptavidin, horseradish peroxidase, or luciferase.

In some aspects, the lipid capsule comprises an outer surface, wherein the outer surface comprises a lipid layer. In some aspects, the lipid layer is a lipid bilayer. In some aspects, the lipid capsule comprises phospholipids. In some aspects, the lipid capsule comprises a polyethylene glycol (PEG) coating. In some aspects, a lipid capsule is identified as comprising a lipid core shell nanostructure. In some aspects, a lipid capsule is composed of an external shell, formed of solid lipids and emulsifying agents, and an oily core, wherein the therapeutic agent is present in the oily core. In some aspects, a lipid capsule comprises a liquid based core, wherein the liquid based core is saline based. For example, the lipid capsule can comprise an ethanol core and external salt solution. In some aspects, the lipid capsule is 5-500 nm. In some aspects, the lipid capsule is 50-400 nm. In some aspects, the lipid capsule is 50-150 nm. In some aspects, the lipid capsule is 100-300 nm.

In some aspects, the target site comprises a cell. For example, the cell can be, but is not limited to, a cancer cell, a pathogen-infected cell, or an immune cell. In some aspects, a cancer cell can be, but is not limited to, a pancreatic cancer cell, glioblastoma cell or lung metastatic carcinoma cell. In some aspects, a pathogen-infected cell can be a virus infected, bacteria infected, or fungus infected cell. In some aspects, the nanoparticle enters the target site. For example, in some aspects, target site is a cancer cell or pathogen-infected cell and the lipid capsule can enter the cancer cell or pathogen-infected cell. In some aspects, the target site is the lungs and the lipid capsule can enter the lungs.

In some aspects, the subject has cancer, an infection, an inflammatory disorder, or is immune suppressed. In some aspects, the therapeutic is an anti-cancer, anti-infectious agent, anti-inflammatory or pro-inflammatory therapeutic.

In some aspects, the frequency of the alternating electric field is between 100 and 500 kHz. In some aspects, the frequency of the alternating electric field is between 180 and 220 kHz. In some aspects, the frequency of the alternating electric field is between 50 and 500 kHz or 50 and 1 MHz.

Also disclosed are methods of treating a subject in need thereof comprising administering a lipid capsule to a target site of a subject, wherein the lipid capsule comprises a therapeutic agent; and applying an alternating electric field, at a frequency for a period of time, to the target site of the subject, wherein the alternating electric field releases the therapeutic from lipid capsule at the target site of the subject, and further comprising applying a second alternating electric field at a second frequency to the target site prior to, during or after the step of administering the lipid capsule to the target site of the subject. In some aspects, disclosed are methods that allow the lipid capsule to get to a target site and the alternating electric fields cause the lipid capsule to increase permeability thus releasing the therapeutic from the lipid capsule near a cell but not within the cell. Also disclosed are methods that allow the lipid capsule to get to a target site and a first alternating electric field causes the lipid capsule to enter a cell and a second alternating electric field causes the nanoparticle to increase permeability thus releasing the therapeutic from the lipid capsule within the cell. In some aspects, the second alternating electric field increases permeability of a cell membrane of a cell at the target site of the subject.

In some aspects, when a second alternating electric field is applied, the first and second alternating electric fields can be at the same frequency or at different frequencies. In some aspects, the first and second alternating electric fields can be at different lengths of time for the same lengths of time.

In some aspects, the lipid capsule is administered prior to exposing the target site to the alternating electric field. In some aspects, the lipid capsule is administered at the same time as the alternating electric field. In some aspects, the lipid capsule is administered after the alternating electric field.

In some aspects, a target site is exposed to a second alternating electric field, wherein one alternating electric field treats cells, such as cancer cells, and one alternating electric field increases permeability of a lipid capsule resulting in the therapeutic agent leaking out of the lipid capsule. In some aspects, the cells can be treated with both alternating electric fields and a therapeutic agent.

G. Methods of Killing Cells

Disclosed are methods of killing a cell comprising administering a lipid capsule to a target site, wherein the lipid capsule comprises a therapeutic agent; and applying an alternating electric field for a period of time, to the target site, wherein the alternating electric field releases the therapeutic agent from the lipid capsule at the target site, wherein the target site comprises a cell, wherein the therapeutic kills the cell.

In some aspects, the disclosed methods of killing a cell occurs in vivo. In some aspects, administering a lipid capsule to a target site comprises administering a lipid capsule to a target site of a subject. In some aspects, the disclosed methods of killing a cell occurs in vitro. In some aspects, administering a lipid capsule to a target site comprises administering a lipid capsule to a culture dish comprising cells.

In some aspects, a cell can be a cancer cell or a pathogen-infected cell. In some aspects, the subject has cancer, an infection, or an inflammatory disorder. In some aspects, the subject has a neurodegenerative disease, autoimmune disease, or orthopedic condition. In some aspects, the infection can be a viral, bacterial or fungal infection. In some aspects, the cancer can be brain cancer, pancreatic cancer, lung cancer, ovarian cancer, or breast cancer. In some aspects, the therapeutic is an anti-cancer, anti-infectious agent, or anti-inflammatory.

In some aspects, the lipid capsule is loaded with a therapeutic agent. In some aspects, the therapeutic agent is encapsulated in the lipid capsule. In some aspects, the lipid capsules can be actively or passively loaded with a therapeutic agent. In some aspects, the lipid capsule is coated with a therapeutic agent. In some aspects, the therapeutic agent is conjugated to the lipid capsule. For example, the conjugation can be via a linker. In some aspects, the linker can be cleavable. There are several ways a lipid capsule can "carry" a therapeutic agent, all of which are considered herein.

In some aspects, the therapeutic agent can be a small molecule, nucleic acid, carbohydrate, lipid, peptide, antibody, or antibody fragment. In some aspects, the therapeutic agent can be any composition capable of treating a disease of interest. For example, a therapeutic agent can be, but is not limited to, an anti-cancer therapeutic, an anti-viral therapeutic, an anti-bacterial therapeutic, an anti-fungal therapeutic, a pro-inflammatory therapeutic, or an anti-inflammatory therapeutic. In some aspects, an anti-cancer therapeutic can be Gemcitabine (GEM), paclitaxel, doxorubicin, cytarabine, daunorubicin, or any chemotherapeutic. In some aspects, a therapeutic agent can be a siRNA, antisense oligonucleotide, or aptamers.

In some aspects, the lipid capsule comprises a cell-specific targeting moiety. In some aspects, the cell-specific targeting moiety can be a cancer cell-specific targeting moiety.

In some aspects, the targeting moiety can direct, or target, the lipid capsule to a specific cell. The cell-specific targeting moiety can be a chemical, compound, peptide or nucleic acid. Examples of targeting moieties include, but art not limited to, molecules that recognize receptors on specific cell types.

In some aspects, the lipid capsule can comprise a cell penetrating peptide. In some aspects, a cell penetrating peptide can facilitate the delivery of the lipid capsule to the cytoplasm of the cell.

In some aspects, the lipid capsule is labeled. As used herein, a label, or detection agent, is any molecule that can be associated with a nanoparticle, directly or indirectly, and which results in a measurable, detectable signal, either directly or indirectly. Many such labels for incorporation into lipid capsule or coupling to lipid capsule are known to those of skill in the art. Examples of detection agents can be, but are not limited to, radioactive isotopes, fluorescent molecules, phosphorescent molecules, enzymes, antibodies, and ligands.

Examples of suitable fluorescent labels include fluorescein (FITC), 5,6-carboxymethyl fluorescein, Texas red, nitrobenz-2-oxa-1,3-diazol-4-yl (NBD), coumarin, dansyl chloride, rhodamine, 4'-6-diamidino-2-phenylinodole (DAPI), and the cyanine dyes Cy3, Cy3.5, Cy5, Cy5.5 and Cy7. Preferred fluorescent labels are fluorescein (5-carboxyfluorescein-N-hydroxysuccinimide ester) and rhodamine (5,6-tetramethyl rhodamine). Preferred fluorescent labels for combinatorial multicolor coding are FITC and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. The fluorescent labels can be obtained from a variety of commercial sources, including Molecular Probes, Eugene, OR and Research Organics, Cleveland, Ohio.

In some instances, a label can be, but is not limited to, an isotope marker, colorimetric biosensors, or fluorescent labels. For example, fluorescent markers can be, but are not limited to, green fluorescent protein (GFP) or rhodamine fluorescent protein (RFP). Other labels can include biotin, streptavidin, horseradish peroxidase, or luciferase.

In some aspects, the lipid capsule comprises an outer surface, wherein the outer surface comprises a lipid layer. In some aspects, the lipid layer is a lipid bilayer. In some aspects, the lipid capsule comprises phospholipids. In some aspects, the lipid capsule comprises a polyethylene glycol (PEG) coating. In some aspects, a lipid capsule is identified as comprising a lipid core shell nanostructure. In some aspects, a lipid capsule is composed of an external shell, formed of solid lipids and emulsifying agents, and an oily core, wherein the therapeutic agent is present in the oily core. In some aspects, a lipid capsule comprises a liquid based core, wherein the liquid based core is saline based. For example, the lipid capsule can comprise an ethanol core and external salt solution.

In some aspects, the lipid capsule is 5-500 nm. In some aspects, the nanoparticle is 50-400 nm. In some aspects, the nanoparticle is 50-150 nm. In some aspects, the nanoparticle is 100-300 nm.

In some aspects, the target site comprises a cell. For example, the cell can be, but is not limited to, a cancer cell, a pathogen-infected cell, or an immune cell. In some aspects, a cancer cell can be, but is not limited to, a pancreatic cancer cell, glioblastoma cell or lung metastatic carcinoma cell. In some aspects, a pathogen-infected cell can be a virus infected, bacteria infected, or fungus infected cell. In some aspects, the nanoparticle enters the target site. For example, in some aspects, target site is a cancer cell or pathogen-infected cell and the nanoparticle can enter the cancer cell or pathogen-infected cell. In some aspects, the target site is the lungs and the nanoparticle can enter the lungs. In some aspects, the target site can comprise fibrotic tissue or cancer tissue. In some aspects, the target site can be a joint.

In some aspects, the subject has cancer, an infection, an inflammatory disorder, or is immune suppressed. In some aspects, the therapeutic is an anti-cancer, anti-infectious agent, anti-inflammatory or pro-inflammatory therapeutic.

In some aspects, the frequency of the alternating electric field is between 100 and 500 kHz. In some aspects, the frequency of the alternating electric field is between 180 and 220 kHz. In some aspects, the frequency of the alternating electric field is between 50 and 500 kHz or 50 and 1 MHz.

Also disclosed are methods of killing a cell comprising administering a lipid capsule to a target site, wherein the lipid capsule comprises a therapeutic agent; and applying an alternating electric field for a period of time, to the target site, wherein the alternating electric field releases the therapeutic agent from the lipid capsule at the target site, wherein the target site comprises a cell, wherein the therapeutic kills the cell, and further comprising applying a second alternating electric field at a second frequency to the target site prior to, during or after the step of administering the lipid capsule to the target site of the subject.

Disclosed are methods that allow the lipid capsule to get to a target site and the alternating electric fields cause the lipid capsule to increase permeability thus releasing the therapeutic from the lipid capsule near a cell but not within the cell. Also disclosed are methods that allow the lipid capsule to get to a target site and a first alternating electric field causes the lipid capsule to enter a cell and a second alternating electric field causes the lipid capsule to increase permeability thus releasing the therapeutic from the lipid capsule within the cell. In some aspects, the second alternating electric field increases permeability of a cell membrane of a cell at the target site of the subject.

In some aspects, when a second alternating electric field is applied, the first and second alternating electric fields can be at the same frequency or at different frequencies. In some aspects, the first and second alternating electric fields can be at different lengths of time for the same lengths of time.

In some aspects, the lipid capsule is administered prior to exposing the target site to the alternating electric field. In some aspects, the lipid capsule is administered at the same time as the alternating electric field. In some aspects, the lipid capsule is administered after the alternating electric field.

In some aspects, a target site is exposed to a second alternating electric field, wherein one alternating electric field kills cells, such as cancer cells, and one alternating electric field increases permeability of a lipid capsule resulting in the therapeutic agent leaking out of the lipid capsule. In some aspects, the cells can be treated with both alternating electric fields and a therapeutic agent.

H. Drug Delivery System

Disclosed are drug delivery systems comprising a lipid capsule comprising a therapeutic agent; and a device capable of administering an alternating electric field.

In some aspects, the lipid capsule is loaded with a therapeutic agent. In some aspects, the therapeutic agent is encapsulated in the lipid capsule. In some aspects, the lipid capsules can be actively or passively loaded with a therapeutic agent. In some aspects, the lipid capsule is coated with a therapeutic agent. In some aspects, the therapeutic agent is conjugated to the lipid capsule. For example, the conjugation can be via a linker. In some aspects, the linker can be cleavable. There are several ways a lipid capsule can "carry" a therapeutic agent, all of which are considered herein.

In some aspects, the therapeutic agent can be a small molecule, nucleic acid, carbohydrate, lipid, peptide, antibody, or antibody fragment. In some aspects, the therapeutic agent can be any composition capable of treating a disease of interest. For example, a therapeutic agent can be, but is not limited to, an anti-cancer therapeutic, an anti-viral therapeutic, an anti-bacterial therapeutic, an anti-fungal therapeutic, a pro-inflammatory therapeutic, or an anti-inflammatory therapeutic. In some aspects, an anti-cancer therapeutic can be Gemcitabine (GEM), paclitaxel, doxorubicin, cytarabine, daunorubicin, or any chemotherapeutic. In some aspects, a therapeutic agent can be a siRNA, antisense oligonucleotide, or aptamers.

In some aspects, the lipid capsule comprises a cell-specific targeting moiety. In some aspects, the cell-specific targeting moiety can be a cancer cell-specific targeting moiety.

In some aspects, the targeting moiety can direct, or target, the lipid capsule to a specific cell. The cell-specific targeting moiety can be a chemical, compound, peptide or nucleic acid. Examples of targeting moieties include, but art not limited to, molecules that recognize receptors on specific cell types.

In some aspects, the lipid capsule can comprise a cell penetrating peptide. In some aspects, a cell penetrating peptide can facilitate the delivery of the nanoparticle to the cytoplasm of the cell.

In some aspects, the lipid capsule is labeled. As used herein, a label, or detection agent, is any molecule that can be associated with a nanoparticle, directly or indirectly, and which results in a measurable, detectable signal, either directly or indirectly. Many such labels for incorporation into lipid capsules or coupling to lipid capsules are known to those of skill in the art. Examples of detection agents can be, but are not limited to, radioactive isotopes, fluorescent molecules, phosphorescent molecules, enzymes, antibodies, and ligands.

Examples of suitable fluorescent labels include fluorescein (FITC), 5,6-carboxymethyl fluorescein, Texas red, nitrobenz-2-oxa-1,3-diazol-4-yl (NBD), coumarin, dansyl chloride, rhodamine, 4'-6-diamidino-2-phenylinodole (DAPI), and the cyanine dyes Cy3, Cy3.5, Cy5, Cy5.5 and Cy7. Preferred fluorescent labels are fluorescein (5-carboxyfluorescein-N-hydroxysuccinimide ester) and rhodamine (5,6-tetramethyl rhodamine). Preferred fluorescent labels for combinatorial multicolor coding are FITC and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. The fluorescent labels can be obtained from a variety of commercial sources, including Molecular Probes, Eugene, OR and Research Organics, Cleveland, Ohio.

In some instances, a label can be, but is not limited to, an isotope marker, colorimetric biosensors, or fluorescent labels. For example, fluorescent markers can be, but are not limited to, green fluorescent protein (GFP) or rhodamine fluorescent protein (RFP). Other labels can include biotin, streptavidin, horseradish peroxidase, or luciferase.

In some aspects, the lipid capsule comprises an outer surface, wherein the outer surface comprises a lipid layer. In some aspects, the lipid layer is a lipid bilayer. In some aspects, the lipid capsule comprises phospholipids. In some aspects, the lipid capsule comprises a polyethylene glycol (PEG) coating. In some aspects, a lipid capsule is identified as comprising a lipid core shell nanostructure. In some aspects, a lipid capsule is composed of an external shell, formed of solid lipids and emulsifying agents, and an oily core, wherein the therapeutic agent is present in the oily core. In some aspects, a lipid capsule comprises a liquid based core, wherein the liquid based core is saline based. For example, the lipid capsule can comprise an ethanol core and external salt solution.

In some aspects, the lipid capsule is 5-500 nm. In some aspects, the lipid capsule is 50-400 nm. In some aspects, the lipid capsule is 50-150 nm. In some aspects, the lipid capsule is 100-300 nm.

In some aspects, a device capable of administering an alternating electric field can be the Optune™ system.

I. Kits

The materials described above as well as other materials can be packaged together in any suitable combination as a kit useful for performing, or aiding in the performance of, the disclosed methods. It is useful if the kit components in a given kit are designed and adapted for use together in the disclosed method. For example disclosed are kits comprising one or more of the disclosed lipid capsules. In some aspects, the kits can comprise the components to create the disclosed lipid capsules.

Disclosed are kits comprising a device capable of administering an alternating electric field and optionally a lipid capsule comprising a therapeutic agent. Disclosed are kits comprising a device capable of administering an alternating electric field and optionally a lipid capsule. In some aspects, the kits further comprise instructions for using the device and/or applying the alternating electrical field to a cell or a subject.

In some aspects the kits disclosed herein can further comprise instructions for using a device capable of administering an alternating electric field in combination with a lipid capsule comprising a therapeutic agent.

In some aspects, the kits disclosed herein can comprise instructions for where to apply the alternating electrical field. In some aspects, the kits disclosed herein can comprise instructions for determining a region-of-interest (ROI) within a 3D model of a portion of a subject's body, determining, based on a center of the ROI, a plane that transverses the portion of the subject's body, wherein the plane comprises a plurality of pairs of positions along a contour of the plane, adjusting, based on an anatomical restriction, one or more positions of the plurality of pairs of positions to generate a modified plane, determining, for each pair of positions of the plurality of pairs positions on the modified plane, a simulated electric field distribution, determining, based on the simulated electric field distributions, a dose metric for each pair of positions of the plurality of pairs positions, determining one or more sets of pairs of positions of the plurality of pairs of positions that satisfy an angular restriction between pairs of transducer arrays, and determining, based on the dose metrics and the one or more sets of pairs of positions that satisfy the angular restriction, one or more candidate transducer array layout maps.

In some aspects, the kits disclosed herein comprise a device capable of administering an alternating electric field, wherein the kit further comprises electrodes for applying the alternating electric field. (e.g. Optune system). In some aspects, the kits disclosed herein can further comprise instructions on where to apply the electrodes to increase the efficacy of alternating electric fields therapy. In some aspects, the kits disclosed herein further comprise instructions for conducting and analyzing measurements to determine where to apply the electrodes or where to apply the alternating electrical field.

J. Embodiments

Embodiment 1. A method of delivering a therapeutic to a target site of a subject comprising: (A) administering a lipid capsule to a target site of a subject, wherein the lipid capsule comprises a therapeutic agent; and (B) applying an alternating electric field, at a frequency for a period of time, to the target site of the subject, wherein the alternating electric field releases the therapeutic from lipid capsule at the target site of the subject.

Embodiment 2. The method of any preceding embodiment, wherein the lipid capsule is loaded with the therapeutic agent.

Embodiment 3. The method of any preceding embodiment, wherein the therapeutic agent is encapsulated in the lipid capsule.

Embodiment 4. The method of any preceding embodiment, wherein the therapeutic agent is conjugated to the lipid capsule.

Embodiment 5. The method of any preceding embodiment, wherein the therapeutic agent is a small molecule, nucleic acid, carbohydrate, lipid, peptide, antibody, or antibody fragment.

Embodiment 6. The method of any preceding embodiment, wherein the lipid capsule is labeled.

Embodiment 7. The method of any preceding embodiment, wherein the lipid capsule comprises an outer surface, wherein the outer surface comprises a lipid layer.

Embodiment 8. The method of embodiment 7, wherein the lipid layer is a lipid bilayer.

Embodiment 9. The method of any preceding embodiment, wherein the lipid capsule comprises phospholipids.

Embodiment 10. The method of embodiments 7-9, wherein the lipid capsule comprises a polyethylene glycol (PEG) coating.

Embodiment 11. The method of any preceding embodiment, wherein the therapeutic is an anti-cancer therapeutic, an anti-viral therapeutic, an anti-bacterial therapeutic, an anti-fungal therapeutic, a pro-inflammatory therapeutic, or an anti-inflammatory therapeutic.

Embodiment 12. The method of embodiment 11, wherein the anti-cancer therapeutic is a chemotherapeutic agent.

Embodiment 13. The method of any preceding embodiment, wherein the lipid capsule comprises a cell-specific targeting moiety.

Embodiment 14. The method of embodiment 13, wherein the cell-specific targeting moiety is a cancer cell-specific targeting moiety.

Embodiment 15. The method of any preceding embodiment, wherein the lipid capsule enters the target site.

Embodiment 16. The method of any preceding embodiment, wherein the subject has cancer, an infection, an inflammatory disorder, or is immune suppressed.

Embodiment 17. The method of any preceding embodiment, wherein the target site comprises a cell.

Embodiment 18. The method of embodiment 17, wherein the cell is a cancer cell, a pathogen-infected cell, or an immune cell.

Embodiment 19. The method of embodiment 18, wherein the cancer cell is a pancreatic cancer cell, glioblastoma cell or lung metastatic carcinoma cell.

Embodiment 20. The method of embodiment 18, wherein the pathogen-infected cell is a virus infected, bacteria infected, or fungus infected cell.

Embodiment 21. The method of embodiments 18-20, wherein lipid capsule enters the cancer cell or pathogen-infected cell.

Embodiment 22. The method of any preceding embodiment, further comprising applying a second alternating electric field at a second frequency to the target site prior to, during or after step a).

Embodiment 23. The method of embodiment 22, wherein the second alternating electric field increases permeability of a cell membrane of a cell at the target site of the subject.

Embodiment 24. The method of any preceding embodiment, wherein the lipid capsule is 50-400 nm.

Embodiment 25. The method of any preceding embodiment, wherein the frequency of the alternating electric field is between 100 and 500 kHz.

Embodiment 26. The method of any preceding embodiment, wherein the frequency of the alternating electric field is between 180 and 220 kHz.

Embodiment 27. The method of any preceding embodiment, wherein the lipid capsule is administered prior to, during or after exposing the target site to the alternating electric field.

Embodiment 28. A method of increasing target site specific release of a therapeutic agent in a subject comprising: (A) administering a lipid capsule to a target site of a subject, wherein the lipid capsule comprises a therapeutic agent; and (B) applying an alternating electric field, at a frequency for a period of time, to the target site of the subject, wherein the alternating electric field releases the therapeutic agent from the lipid capsule at the target site of the subject, thereby increasing the target site specific release of the therapeutic agent.

Embodiment 29. A method of treating a subject in need thereof comprising (A) administering a lipid capsule to a target site of a subject in need thereof, wherein the lipid capsule comprises a therapeutic agent; and (B) applying an alternating electric field, at a frequency for a period of time, to the target site of the subject in need thereof, wherein the alternating electric field releases the therapeutic agent from the lipid capsule at the target site of the subject in need thereof.

Embodiment 30. The method of embodiment 29, wherein the subject in need thereof has cancer, an infection, or an inflammatory disorder.

Embodiment 31. The method of embodiment 30, wherein the infection is a viral, bacterial or fungal infection.

Embodiment 32. The method of embodiment 30, wherein the cancer is brain cancer, pancreatic cancer, lung cancer, ovarian cancer, or breast cancer.

Embodiment 33. A method of killing a cell comprising (A) administering a lipid capsule to a target site, wherein the lipid capsule comprises a therapeutic agent; and (B) applying an alternating electric field for a period of time, to the target site, wherein the alternating electric field releases the therapeutic agent from the lipid capsule at the target site, wherein the target site comprises a cell, wherein the therapeutic kills the cell.

Embodiment 34. The method of embodiment 33, wherein administering a lipid capsule to a target site comprises administering a nanoparticle to a target site of a subject.

Embodiment 35. The method of embodiments 33-34, wherein the cell is a cancer cell or a pathogen-infected cell.

Embodiment 36. The method of embodiments 28-35, wherein the lipid capsule is loaded with the therapeutic agent.

Embodiment 37. The method of embodiments 28-35, wherein the therapeutic agent is encapsulated in the lipid capsule.

Embodiment 38. The method of embodiments 28-35, wherein the therapeutic agent is conjugated to the lipid capsule.

Embodiment 39. The method of embodiments 28-38, wherein the therapeutic agent is a small molecule, nucleic acid, carbohydrate, lipid, peptide, antibody, or antibody fragment.

Embodiment 40. The method of embodiments 28-39, wherein the lipid capsule is labeled.

Embodiment 41. The method of embodiments 28-40, wherein the lipid capsule comprises an outer surface, wherein the outer surface comprises a lipid layer Embodiment 42. The method of embodiments 28-41, wherein the lipid layer is a lipid bilayer.

Embodiment 43. The method of embodiments 41-42, wherein the lipid capsule comprises phospholipids.

Embodiment 44. The method of embodiments 41-43, wherein the lipid capsule comprises a polyethylene glycol (PEG) coating.

Embodiment 45. The method of embodiments 28-45, wherein the therapeutic is an anti-cancer therapeutic, an anti-viral therapeutic, an anti-bacterial therapeutic, an anti-fungal therapeutic, a pro-inflammatory therapeutic, or an anti-inflammatory therapeutic.

Embodiment 46. The method of embodiment 45, wherein the anti-cancer therapeutic is a chemotherapeutic agent.

Embodiment 47. The method of embodiments 28-46, wherein the lipid capsule comprises a cell-specific targeting moiety.

Embodiment 48. The method of embodiments 47, wherein the cell-specific targeting moiety is a cancer cell-specific targeting moiety.

Embodiment 49. The method of embodiments 28-48, wherein the lipid capsule enters the target site.

Embodiment 50. The method of embodiments 28-49, wherein the subject has cancer, an infection, an inflammatory disorder, or is immune suppressed.

Embodiment 51. The method of embodiments 28-50, wherein the target site comprises a cell.

Embodiment 52. The method of embodiment 51, wherein the cell is a cancer cell, a pathogen-infected cell, or an immune cell.

Embodiment 53. The method of embodiment 52, wherein the cancer cell is a pancreatic cancer cell, glioblastoma cell or lung metastatic carcinoma cell.

Embodiment 54. The method of embodiment 52, wherein the pathogen-infected cell is a virus infected, bacteria infected, or fungus infected cell.

Embodiment 55. The method of embodiments 52-54, wherein the lipid capsule enters the cancer cell or pathogen-infected cell.

Embodiment 56. The method of embodiments 28-55, further comprising applying a second alternating electric field at a second frequency to the target site prior to, during or after step a).

Embodiment 57. The method of embodiments 56, wherein the second alternating electric field increases permeability of a cell membrane of a cell at the target site of the subject.

Embodiment 58. The method of embodiments 28-57, wherein the lipid capsule is 50-400 nm.

Embodiment 59. The method of embodiments 28-58, wherein the frequency of the alternating electric field is between 100 and 500 kHz.

Embodiment 60. The method of embodiments 28-59, wherein the frequency of the alternating electric field is between 180 and 220 kHz.

Embodiment 61. The method of embodiments 28-60, wherein the lipid capsule is administered prior to, during or after exposing the target site to the alternating electric field.

Embodiment 62. A drug delivery system comprising: (A) a lipid capsule comprising a therapeutic agent; and (B) a device capable of administering an alternating electric field.

Embodiment 63. A kit comprising: (A) a lipid capsule comprising a therapeutic agent; and (B) a device capable of administering an alternating electric field.

Embodiment 64. The method of embodiment 40, further comprising instructions for using the device.

Those skilled in the art will recognize, or be able to ascertain using no more than routine experimentation, many equivalents to the specific embodiments of the method and compositions described herein. Such equivalents are intended to be encompassed by the following claims.

We claim:

1. A method of delivering a therapeutic to a target site of a subject comprising:
   a. administering a lipid capsule to a target site of a subject, wherein the lipid capsule comprises a therapeutic agent; and
   b. applying an alternating electric field, at a frequency for a period of time, to the target site of the subject, wherein the alternating electric field releases the therapeutic from the lipid capsule at the target site of the subject.

2. The method of claim 1, wherein the lipid capsule is loaded with the therapeutic agent.

3. The method of claim 1, wherein the therapeutic agent is encapsulated in the lipid capsule.

4. The method of claim 1, wherein the therapeutic agent is conjugated to the lipid capsule.

5. The method of claim 1, wherein the therapeutic agent is a small molecule, nucleic acid, carbohydrate, lipid, peptide, antibody, or antibody fragment.

6. The method of claim 1, wherein the lipid capsule comprises an outer surface, wherein the outer surface comprises a lipid layer.

7. The method of claim 6, wherein the lipid layer is a lipid bilayer.

8. The method of claim 1, wherein the lipid capsule comprises phospholipids.

9. The method of claim 1, wherein the therapeutic is an anti-cancer therapeutic, an anti-viral therapeutic, an anti-bacterial therapeutic, an anti-fungal therapeutic, a pro-inflammatory therapeutic, or an anti-inflammatory therapeutic.

10. The method of claim 9, wherein the anti-cancer therapeutic is a chemotherapeutic agent.

11. The method of claim 1, wherein the lipid capsule enters the target site.

12. The method of claim 1, wherein the subject has cancer, an infection, an inflammatory disorder, or is immune suppressed.

13. The method of claim 1, wherein the target site comprises a cell.

14. The method of claim 13, wherein the cell is a cancer cell, a pathogen-infected cell, or an immune cell.

15. The method of claim 13, wherein the lipid capsule enters the cancer cell or pathogen-infected cell prior to releasing the therapeutic.

16. The method of claim 1, further comprising applying a second alternating electric field at a second frequency to the target site prior to, during or after step a).

17. The method of claim 1, wherein the frequency of the alternating electric field is between 100 and 500 kHz.

18. The method of claim 1, wherein the lipid capsule is administered prior to, during or after exposing the target site to the alternating electric field.

19. A method of increasing target site specific release of a therapeutic agent in a subject comprising:
   a. administering a lipid capsule to a target site of a subject, wherein the lipid capsule comprises a therapeutic agent; and
   b. applying an alternating electric field, at a frequency for a period of time, to the target site of the subject, wherein the alternating electric field releases the therapeutic agent from the lipid capsule at the target site of the subject, thereby increasing the target site specific release of the therapeutic agent.

20. A method of treating a subject in need thereof comprising
   a. administering a lipid capsule to a target site of a subject in need thereof, wherein the lipid capsule comprises a therapeutic agent; and
   b. applying an alternating electric field, at a frequency for a period of time, to the target site of the subject in need thereof, wherein the alternating electric field releases the therapeutic agent from the lipid capsule at the target site of the subject in need thereof.

* * * * *